United States Patent [19]

Lindstrom

[11] Patent Number: 4,799,931
[45] Date of Patent: Jan. 24, 1989

[54] INTRACORNEAL LENS

[76] Inventor: Richard L. Lindstrom, 1065 W. Ferndale Rd., Wayzata, Minn. 55391

[21] Appl. No.: 863,049

[22] Filed: May 14, 1986

[51] Int. Cl.$^4$ .................................................. A61F 2/4
[52] U.S. Cl. ....................................................... 623/5
[58] Field of Search ........................................ 623/4-6; 128/1 R

[56] References Cited

U.S. PATENT DOCUMENTS

| | | | |
|---|---|---|---|
| 2,517,523 | 8/1950 | Batchelder | 623/6 |
| 2,952,023 | 9/1960 | Rosen | 623/4 |
| 3,945,054 | 3/1976 | Federov et al. | 623/6 |
| 4,563,779 | 1/1986 | Kelman | 623/5 |
| 4,624,669 | 11/1986 | Grendahl | 623/5 |
| 4,655,774 | 4/1987 | Choyce | 623/5 |
| 4,693,939 | 9/1987 | Ofstead | 623/5 |

FOREIGN PATENT DOCUMENTS 2705234  8/1978  Fed. Rep. of Germany .......... 623/5

Primary Examiner—Ronald L. Frinks
Attorney, Agent, or Firm—Hugh D. Jaeger

[57] ABSTRACT

An intracorneal lens with at least one hole such as central pinhole, or a, plurality of pinholes or the like; and, a material filling the holes or a material filling the pinholes, and coating the lens. The intracorneal lens can be of any high index of refraction material. The material filling the holes as well as coating the lens can be a gas permeable polymer or metabolite permeable material, a biocompatible polymer or biocompatible material, or a neutral or negatively charged material.

3 Claims, 4 Drawing Sheets

INTRACORNEAL LENS

BACKGROUND OF THE INVENTION

1. Field of the Invention

The present invention pertains to an intracorneal lens, and more particularly, pertains to an intracorneal lens including one or holes where the holes are filled with a gas permeable polymer or metabolite permeable material, a biocompatible polymer or biocompatible material, or a neutral or negatively charged material. The intracorneal lens can also include a coating of a gas permeable polymer or metabolite permeable material, a biocompatible polymer or biocompatible material, or neutral or negatively charged material.

2. Description of the Prior Art

Intracorneal lenses, also known as corneal inlays or intralamellar lenses, are known in the art. It has been desirable to provide intracorneal lenses with holes to provide for passage of nutrients and fluids. It has now been recognized that it may be suitable to fill the holes with a material as well as coating the lens with a material.

The present invention provides an intracorneal lens with holes, where the holes are filled with the gas permeable polymer or metabolite permeable material, a biocompatible polymer or biocompatible material, or a neutral or negatively charged material. The intracorneal lens can also be coated with the gas permeable polymer or a metabolite permeable material, a biocompatible polymer or biocompatible material, or a neutral or negatively charged material.

SUMMARY OF THE INVENTION

The general purpose of the present invention is to provide an intracorneal lens with one or more holes, the holes being filled with a gas permeable polymer or a metabolite permeable material, a biocompatible polymer or biocompatible material, or a neutral or negatively charged material. The lens can also be coated with a gas permeable polymer or a metabolite permeable material, a biocompatible polymer or biocompatible material, or a neutral or negatively charged material.

According to one embodiment of the present invention, there is provided an intracorneal lens with one or more holes, the plurality of holes filled with a gas permeable polymer or a metabolite permeable material, a biocompatible polymer or biocompatible material, or a neutral or negatively charged material. The lens can also be coated with a gas permeable polymer or a metabolite permeable polymer accordingly, a biocompatible polymer or biocompatible material, or a neutral or negatively charged material. The intracorneal lens would be of a high index of refraction material. The hole material and coating would either be a gas permeable polymer or a metabolite permable material, a biocompatible polymer or biocompatible material, or a neutral or negatively charged material.

DESCRIPTION OF THE PREFERRED EMBODIMENTS

Figure 1:
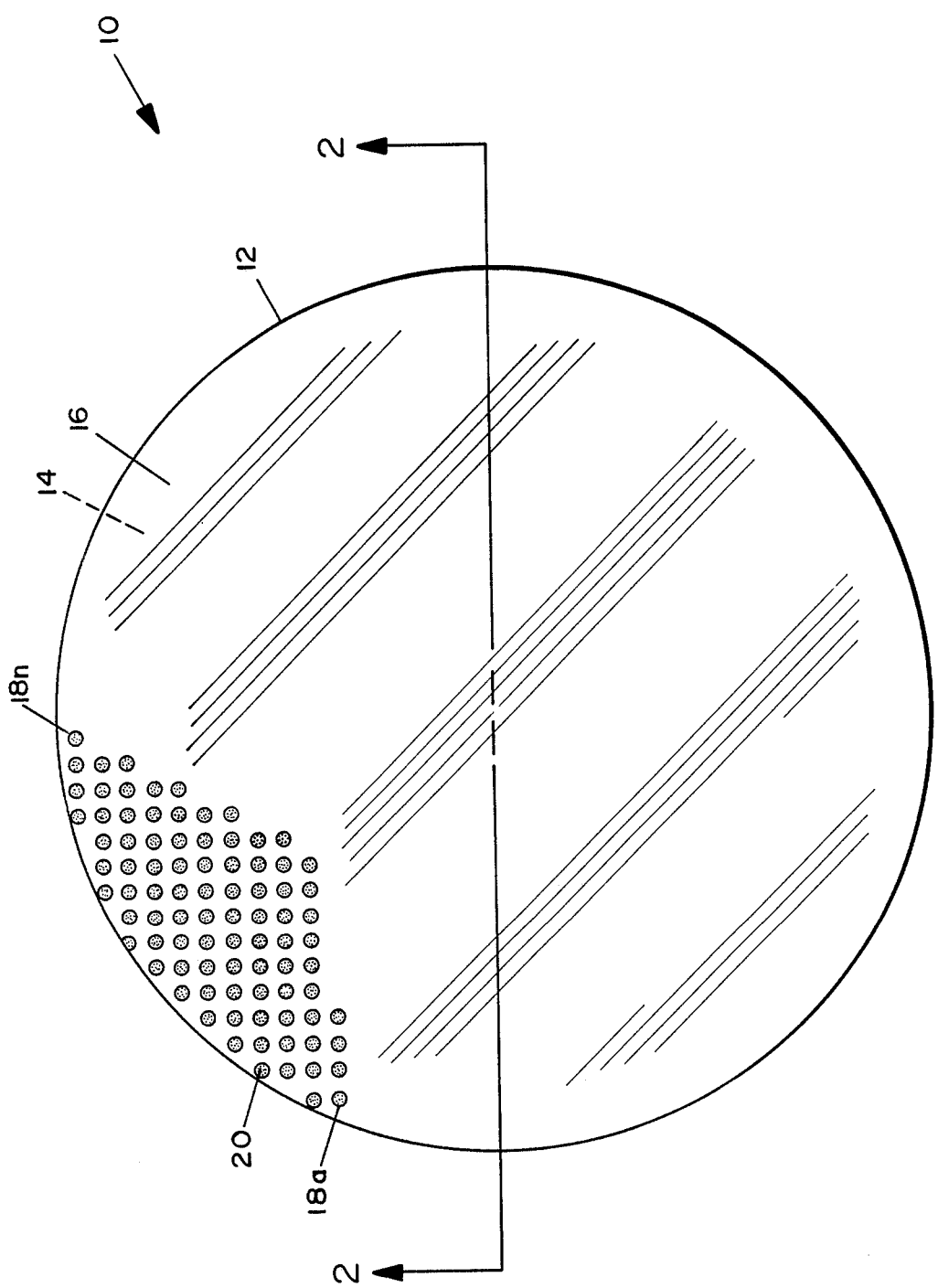
FIG. 1 illustrates a top view of an intracorneal lens with holes and a material filling the holes.

FIG. 1 illustrates an intracorneal lens 10, including an edge 12, a posterior surface 14 and an anterior surface 16. The corneal lens can be made of any high index of refraction material such as a polymer, polysulfone, polyether ketone, polycarbonate, or like material. The corneal inlay is provided with either a single pinhole such as in the center of the lens, or a plurality of holes 18a–18n as illustrated in the figure. There can be a single pinhole in the lens such as 0.01 to 1 millimeter in diameter, or a plurality of holes such as 0.000001 millimeter to 1 millimeter diameter. The dimensions for each hole are by way of example and for purposes of illustration, and not to be construed as limiting of the present invention. The lens can be provided with a single pinhole such as in the center or with a plurality of multiple holes as illustrated in FIG. 1. The holes can also be filled with either a gas permeable polymer such as silicone, hydrogel, cellulose acetate butyrate, or a metabolite permeable substance. The holes are filled with either metabolite material or gas permeable material, a biocompatible polymer or biocompatible material, or a neutral or negatively charged material. The material 20 is illustrated in FIGS. 1 and 2.

Figure 2:
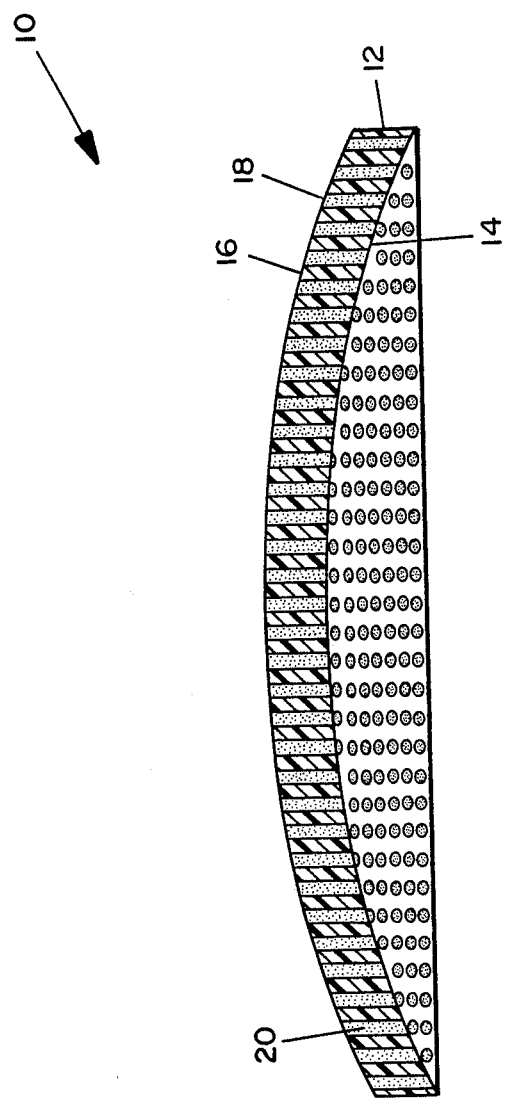
FIG. 2 illutrates a sectional a view along the line 2—2 of FIG. 1.

FIG. 2 illustrates a view taken along line 2—2 of the intracorneal lens with holes, the holes being filled with either the metabolite material or the gas permeable polymer, the biocompatible polymer or biocompatible material, or the neutral or negatively charged material.

Figure 3:
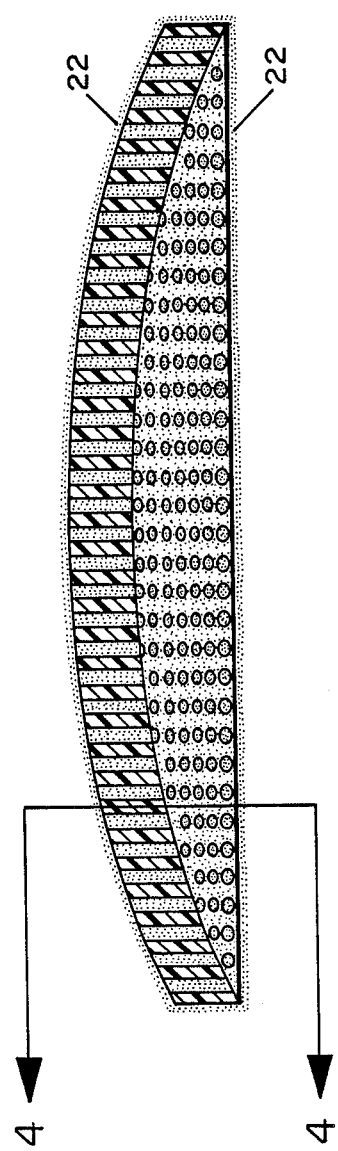
FIG. 3 illustrates a side view of an intracorneal lens with material filling the holes and coating the lens; and, FIG. 4 illustrates an enlarged view along line 4—4 of FIG. 3 showing a view of the material filling the holes and coating the lens.

FIG. 3 illustrates an intracorneal lens where the holes have been filled, and the lens has been coated with either the same material as that filling the holes or a different like material from the group of materials previously set forth in FIGS. 1 and 2. The coating 22 is on the anterior surface as well as the posterior surface of the intracorneal lens, although the coating could be on only either one or the other of the surface of the lens or on the edge. The coating is illustrated as extending around the edge of the lens.

Figure 4:
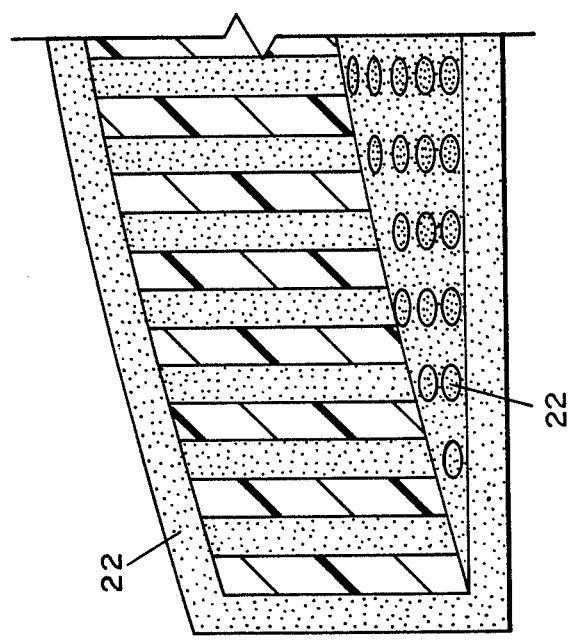

FIG. 4 illustrates a enlarged view where the coating is on both surfaces of the lens as well as through the holes of the lens.

The intracorneal lens can also be hole free, and the metabolite permeable or the gas permeable material, the biocompatible polymer or biocompatible material, or the neutral or negatively charged material can be on any surface of the lens or even all of the surfaces of the lens.

MODE OF OPERATION

The metabolite permeable material or the gas permeable polymer, the biocompatible polymer or the biocompatible material, or the neutral or negatively charged material allows for the passage of fluids and gases as well as nutrients through the material in the holes as well as the coatings of the lens as well as through the surfaces of the lens.

Various modifications can be made to the present invention without departing from the apparent scope thereof.

I claim:

1. Intracorneal lens comprising:

a. intracorneal lens optic of a high index of refraction polymer material selected from the group consisting of polysulfone, polyether ketone, or polycarbonate, the optic including a plurality of holes of a diameter in the range of 0.00001 mm to 1 mm; and, b. a gas permeable biocompatible material coating on at least a portion of said lens and filling said holes, said coating and said filling material being selected from the group consisting of silicon, hydrogel or cellulose acetate butyrate.

2. Intracorneal lens of claim 1 wherein said coating is on both sides of said lens and in said holes of said lens.

3. Intracorneal lens of claim 1 wherein said material in said holes and said material coating said lens are different materials.

* * * * *